United States Patent [19]

Foley

[11] 4,259,493

[45] Mar. 31, 1981

[54] PERHALOMETHYLCARBINOL-SUBSTITUTED PHENOL AND NAPHTHOL SULFAMPHTHALEINS

[75] Inventor: James W. Foley, Andover, Mass.

[73] Assignee: Polaroid Corporation, Cambridge, Mass.

[21] Appl. No.: 957,163

[22] Filed: Nov. 2, 1978

[51] Int. Cl.³ .................. C07D 455/02; C07D 275/06; C07D 279/02; C07D 417/10
[52] U.S. Cl. ..................................... 546/96; 252/300; 430/517; 430/520; 430/560; 260/245.5; 260/338; 548/207; 544/33; 544/62; 546/198; 546/95; 544/133; 544/135; 544/368
[58] Field of Search ................. 544/33, 133, 135, 62, 544/368; 546/95, 198, 96; 260/239 R, 301, 304, 245.5; 548/207

[56] References Cited

PUBLICATIONS

Abramovitch, R., J. Chem. Soc., Perkin Trans I, 1974 (22) p. 2589.
Mustafa, A., J. Chem. Soc. (1952), p. 1339.
Dutt, J. Chem. Soc., 121, p. 2389 (1922).
Beilstein, "Handbuch der Organischen Chemie, vol. 27, p. 534.
Suzuki, "Electron Absorption Spectra and Geometry of Organic Molecules", 1967, p. 406.

Breslow, "Organic Reaction Mechanism" 1969, pp. 114-116.

*Primary Examiner*—Mark L. Berch
*Attorney, Agent, or Firm*—Sybil A. Campbell

[57] ABSTRACT pg,1 The present invention is concerned with novel 3,3-disubstituted-sulfam(na)phthaleins wherein one of the 3-substituents is derived from a 1-naphthol or a phenol substituted in the 2-position with a perhalomethylcarbinol group and wherein the N atom of the sulfam(na)phthalein ring is substituted with

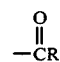

wherein R is alkyl or aryl or with

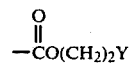

wherein Y is hydrogen or an electron-withdrawing group, which compounds find utility, e.g., as pH-sensitive indicator dyes or as photographic light-screening dyes.

14 Claims, No Drawings

PERHALOMETHYLCARBINOL-SUBSTITUTED PHENOL AND NAPHTHOL SULFAMPHTHALEINS

BACKGROUND OF THE INVENTION

1. Field of the Invention

This invention relates to novel chemical compounds, and more particularly, it relates to novel sulfam(na)phthaleins derived from perhalomethylcarbinol-substituted naphthols and phenols which are useful as indicator dyes or as light-screening dyes in photographic products and processes.

2. Description of the Prior Art

It is well known that photographic film, and especially multicolor films, may and generally do vary from lot to lot, notwithstanding efforts to "repeat" previous films. Manufacturers of multicolor photographic films have developed a number of procedures to minimize the effects upon the final multicolor image of unavoidable variations in the manufacturing operations. These variations are reflected primarily in shifts in color balance as reflected in mismatching of the D log E curves of the individual red, green and blue exposures. Equipment used to coat multicolor films is highly precise but variations between intended coverage of silver halide and/or the dye image-forming materials do occur. Repeat batches of silver halide emulsions may, and usually do, vary in their photographic response. Individual layers may be dried to slightly different degrees. Films are stored for a period of time after coating to allow the films to "age", so that changes in sensitometry following coating have an opportunity to reach a plateau prior to sale. If the film is designed to be developed by a photofinisher or in a darkroom, processing of the exposed multicolor film is controlled within very narrow limits, typically within plus or minus a half degree of a prescribed temperature, in order to minimize sensitometric variations from film to film. Where the multicolor film is of the negative type, an opportunity to adjust the sensitometry occurs in printing the desired final positive image, during which operation the printing exposure may be appropriately color filtered.

The basic sources of sensitometric variations noted above exist also in multicolor diffusion transfer films, with the added complication that once the film is shipped, the sensitometric properties are essentially fixed. The opportunity for adjustment provided in darkroom processing, practically speaking, is unavailable for users of self-developing films. While professional and advanced amateur photographers may be skillful enough to utilize color correction filters to at least partially "rebalance" the color balance, ordinary users of the film would only be confused by such additional operations.

It is well known to use light-screening dyes in photographic elements. Such a dye may be incorporated as a filter dye in a light-sensitive emulsion layer(s) or in a layer coated over one or more light-sensitive emulsion layers or between two differently color-sensitized emulsion layers to modify the light record in the emulsion layer or to control the spectral composition of light falling on the underlying light-sensitive layer, or it may be incorporated as an antihalation dye in a non-light-sensitive layer positioned on either side of a support carrying the light-sensitive layer(s).

The dyes employed for these purposes, in addition to having the requisite spectral absorption characteristics for their intended use, should be photochemically inert, that is, they should not have any adverse effect on the properties of the light-sensitive emulsion layer(s), and also, they should be capable of being decolorized or removed during photographic processing so as not to leave stain in the processed photographic element. In photographic processes where the dye is removed by being dissolved in a processing solution, it is usually preferred that the dye also decolorize in order to avoid contamination of the processing solution and to prevent staining from residual dye in the processed light-sensitive element.

Though various classes of dyes have been proposed for use in antihalation and color correction filter layers, the dyes heretofore employed have not been altogether satisfactory. Some of the dyes tend to reduce sensitivity, fog or exert other adverse effect on the light-sensitive material. However, the major drawback of previously employed dyes is their tendency to cause stain due to incomplete decolorization or reversal of some of the decolorized form to the original colored form. For example, some classes of dyes rely on the presence of a reagent, such as, a sulfite for "bleaching", i.e., decolorization and unless the dyes are removed from the light-sensitive material during or after processing, their color may reappear with a reduction in sulfite concentration.

Copending U.S. Patent Applications Ser. Nos. 835,998 now No. 4,178,446; 836,005; 836,009; and 836,021 now No. 4,204,061 of Stanley M. Bloom, Alan L. Borror and James W. Foley, all filed September 23, 1977, are directed to 3,3-disubstituted-sulfam(na)phthaleins possessing as a 2-substituent, respectively, a —CO$_2$(CH$_2$)$_2$Y moiety wherein Y is an electron-withdrawing group; a

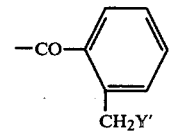

moiety wherein Y' is bromo or chloro; a —CO$_2$R' moiety wherein R' is substituted or unsubstituted alkyl or phenyl; and a —COR" moiety wherein R" is substituted or unsubstituted alkyl or phenyl. In these 2-substituted-sulfam(na)phthaleins, one of the 3-substituents may be a 4'-hydroxy-1'-phenyl moiety or a 4'-hydroxy-1'-naphthyl moiety and the other 3-substituent may be, for example, a phenyl moiety unsubstituted or substituted with one or more groups, such as, hydroxy, alkyl, alkoxy, dialkylamino or a fused substituent, e.g., [ij]-quinolizidine.

As discussed in the aforementioned applications, such compounds have a colorless form below a given alkaline pH and in the presence of base above said alkaline pH, generate a colored, i.e., light-absorbing form. Depending upon the 2-substituent of the sulfam(na)phthalein ring, some of the compounds function as classical pH-sensitive dyes and the light-absorbing form is decolorized by reversal to the original colorless precursor which is effected by reducing the pH below said alkaline pH. The remaining compounds are rendered colorless without reversal to the original colorless precursor and without a pH reduction and decolorize by undergoing an irreversible cleavage reaction with base at a pH above said alkaline pH to yield a colorless product.

The present invention is concerned with a novel class of sulfam(na)phthaleins derived from 2-perhalomethyl-carbinol-substituted 1-naphthols or phenols. In a preferred embodiment, the present invention is concenred with sulfam(na)phthaleins that are initially colored and which find utility as light-screening dyes in photography.

SUMMARY OF THE INVENTION

It is therefore the primary object of the present invention to provide novel sulfam(na)phthaleins.

It is another object of the present invention to provide certain 1-naphthol sulfam(na)phthaleins useful as light-screening dyes in photographic products and processes.

Other objects of this invention will in part be obvious and will in part appear hereinafter.

This invention accordingly comprises the products and compositions possessing the features, properties and the relation of elements which are exemplified in the following detailed disclosure, and the scope of the application of which will be indicated in the claims.

According to the present invention, novel 2-Z-3,3-disubstituted sulfam(na)phthaleins are provided wherein one 3-substituent is a 4'-hydroxy-1'-naphthyl moiety substituted in the 3'-position with a perhalomethylcarbinol group or a 4'-hydroxy-1'-phenyl moiety substituted in the 3'-position with a perhalomethylcarbinol group, the other 3-substituent is, for example, a phenyl moiety substituted or unsubstituted and Z is

wherein R is alkyl or aryl or

wherein Y is hydrogen or an electron-withdrawing group. These compounds will be defined with greater particularity hereinafter.

For a fuller understanding of the nature and objects of the present invention, reference should be had to the following detailed description.

DETAILED DESCRIPTION OF THE INVENTION

The novel compounds provided by the present invention may be represented by the formula

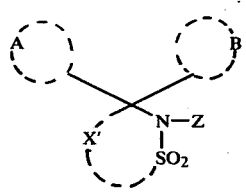

(I)

wherein A is selected from (a) a 4'-hydroxy-1'-naphthyl moiety substituted in the 3'-position with a group,

wherein $R^I$ is perhalomethyl and $R^{II}$ is hydrogen or perhalomethyl, and (b) a 4'-hydroxy-1'-phenyl moiety substituted in the 3'-position with a group,

wherein $R^I$ is perhalomethyl and $R^{II}$ is hydrogen or perhalomethyl; B is a phenyl moiety or a naphthyl moiety provided B is a phenyl moiety when said A is said 4'-hydroxy-1'-naphthyl moiety; X' represents the atoms necessary to complete a ring-closing moiety selected from a sulfamphthalein moiety and a sulfamnaphthalein moiety; and Z is a group selected from

wherein R is alkyl or aryl and

wherein Y is hydrogen or an electron-withdrawing group. By "electron-withdrawing group" is meant a group having a positive sigma value as defined by Hammett's Equation.

Preferred perhalomethyl groups include trifluoromethyl, difluoromethyl, difluorochloromethyl, dichlorofluoromethyl, dichloromethyl and trichloromethyl.

By "sulfamphthalein" is intended a 2,3-dihydrobenz[d]isothiazole-1,1-dioxide moiety and by "sulfamnaphthalein" is intended a 2,3-dihydronaphtho[1,8-de]-1,2-thiazine-1,1-dioxide moiety. The respective 2,3-dihydrobenz[d]isothiazole-1,1-dioxide and 2,3-dihydronaphtho[1,8-de]-1,2-thiazine-1,1-dioxide ring-closing moieties are illustrated below:

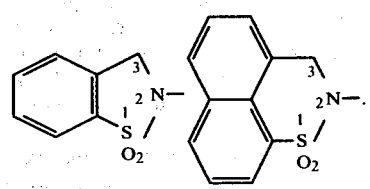

It will be understood that the A moiety and/or the B moiety and/or the ring-closing moiety of the compounds represented in formula I above may contain one or more substituents in addition to those specified, which substituents should not interfere with the intended use of the compounds.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenylsubstituted alkyl, such as p-ethylphenyl, p-octylphenyl, p-dodecylphenyl, benzyl, phenethyl, phenylhexyl and phenyldodecyl; alkoxy, such as, methoxy, ethoxy, butoxy, octadecyloxy, 1-ethoxy-2-(β-ethoxyethoxy); aryloxy, such as, phenoxy, benzyloxy and naphthoxy; alkoxyalkyl, such as, methoxymethyl, ethoxymethyl, and dodecyloxyethyl; halo, such as, fluoro, bromo and chloro; trihalomethyl, such as, trifluoromethyl and trichloromethyl; sulfonamido (—NH—SO₂R° wherein R° is alkyl, aryl, alkaryl or aralkyl); sulfamoyl (—SO₂—NH—R° wherein R° has the same meaning given above); acyl

wherein R° has the meaning given above); sulfonyl (—SO₂—R° wherein R° has the same meaning given above); sulfo; cyano; carboxy, hydroxy; and amino including mono- and disubstituted amino (—NR'R" wherein R' and R" each are hydrogen, alkyl, aryl, alkaryl or aralkyl and R' and R" taken together represent the atoms necessary to complete a saturated heterocyclic ring, such as piperidino, pyrrolidino, N-lower alkylpiperazino, morpholino, thiomorpholino and tetrahydro-2H,4H-1,3,6-dioxazocino or a fused heterocyclic ring system, e.g., quinolizidine).

Preferred compounds within Formula I are those represented by the formula

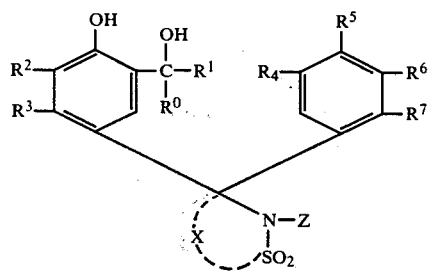

wherein R⁰ is perhalomethyl selected from trifluoromethyl, difluoromethyl, difluorochloromethyl, dichlorofluoromethyl, dichloromethyl and trichloromethyl; R¹ is selected from hydrogen and perhalomethyl having the same meaning given above; R² is hydrogen or methyl; R³ is hydrogen, alkyl or alkoxy; R² and R³ taken together represent the carbon atoms necessary to complete a fused benzene ring; R⁴ and R⁶ each are selected from hydrogen, alkyl, alkoxy, chloro and fluoro; R⁷ is hydrogen, hydroxy, alkyl or alkoxy; R⁶ and R⁷ taken together represent the carbon atoms necessary to complete a fused benzene ring provided R² and R³ are taken separately when R⁶ and R⁷ are taken together; R⁵ is selected from hydrogen, hydroxy, alkyl, alkoxy, —N,N—(dialkyl)amino, —N,N—(w—R⁸alkyl)₂-amino wherein R⁸ is hydroxy or halo, preferably chloro; —NHCOCH₃, piperidino, pyrrolidino, N-methylpiperazino, morpholino, thiomorpholino or tetrahydro-2H,4H-1,3,6-dioxazocino; R⁴, R⁵ and R⁶ taken together represent the atoms necessary to complete a fused [ij]quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide; and Z has the same meaning given in formula I Usually R of said

when alkyl contains 1 to 7 carbon atoms, for example, methyl, ethyl, isopropyl, s-butyl, n-butyl, hexyl or benzyl and preferably is methyl and when aryl preferably is phenyl. When Y of said

is an electron-withdrawing group, it preferably has a positive sigma value greater than 0.6. Preferred electron-withdrawing groups include nitro; cyano; —SO₂CH₃;

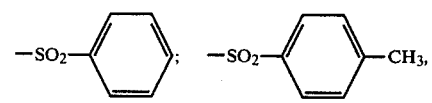

—COCH₃; and —SO₂N(CH₂Ph)₂. The sigma value for these and other groups have been reported by Eugen Müller, Methoden Der Organischen Chemie, Georg Thieme Verlag, Stuttgart, 1970, p. 78.

Usually, the alkyl and alkoxy substituents comprising R³, R⁴, R⁵, R⁶ and R⁷ are lower alkyl having 1 to 4 carbon atoms, such as, methyl, ethyl, n-propyl, isopropyl, s-butyl and n-butyl and lower alkoxy having 1 to 4 carbon atoms, such as, methoxy, ethoxy, propoxy and butoxy. Also, the alkyl groups of the -N,N-(dialkyl)amino each are usually alkyl having 1 to 4 carbon atoms and similarly, the alkyl groups of the —N,N—(w—R⁸—alkyl)₂amino usually contain 1 to 4 carbon atoms. The perhalomethyl groups comprising R⁰ and R¹ may be the same or different and usually are the same.

In a particularly preferred embodiment, the compounds of the present invention may be represented by the formula

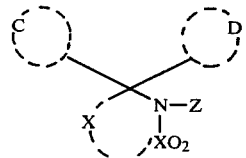

wherein C is a 4'-hydroxy-1'-naphthyl moiety substituted in the 3-position with a group,

wherein R' is perhalomethyl and R'' is hydrogen or perhalomethyl; D is a phenyl moiety substituted with an electron-donating substituent, said D moiety being sufficiently electron donating to give a compound having an epsilon of at least 4000 in the visible wavelength range as measured in trifluoroethanol and preferably, also having a λmax greater than 550 nm as measured in trifluoroethanol; and X and Z have the same meaning given above.

Besides being substituted with one or more electron-donating substituents, the phenyl moiety comprising D may contain substituents that are not electron-donating provided that the overall electron donating properties of the D moiety are sufficient to meet the criterion of giving a compound having an epsilon of at least 4000 in the visible wavelength range, i.e., 400 to 700 nm. By an electron-donating substituent is meant a substituent having a negative sigma value as defined by Hammett's Equation. Typical electron-donating substituents include -N,N-(dialkyl)amino, pyrrolidino and fused substituents, e.g., a fused [ij]quinolizidine ring.

Preferred compounds within formula III are those of the following formula

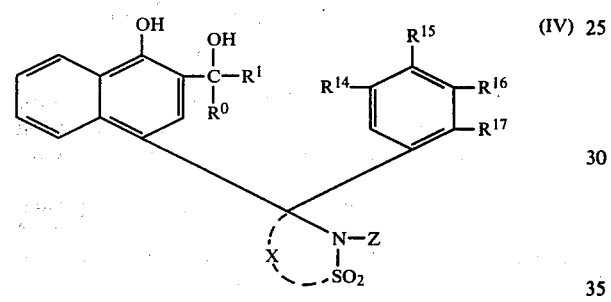

(IV)

wherein $R^0$, $R^1$, X and Z have the same meaning given above; $R^{14}$ and $R^{16}$ are hydrogen, chloro, fluoro, alkoxy or alkyl; $R^{15}$ is pyrrolidino, —N,N—(dialkyl)amino, —N,N—(w-$R^8$alkyl)$_2$amino wherein $R^8$ is halo or hydroxy; and $R^{14}$, $R^{15}$ and $R^{16}$ taken together represent the atoms necessary to complete a fused [ij]quinolizidine ring.

In a particularly preferred embodiment, X represents the atoms necessary to complete 2,3-dihydrobenz[d]isothiazole-1,1-dioxide.

Specific examples of compounds within the scope of the present invention are as follows:

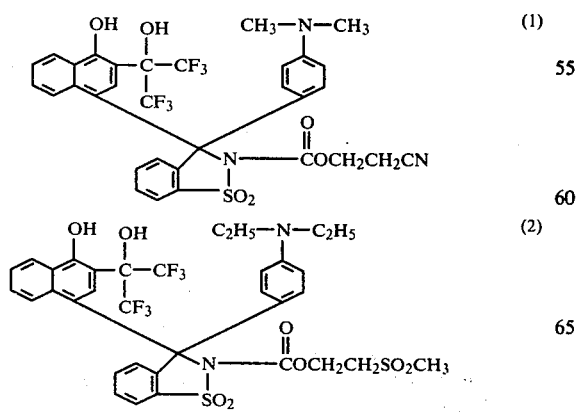

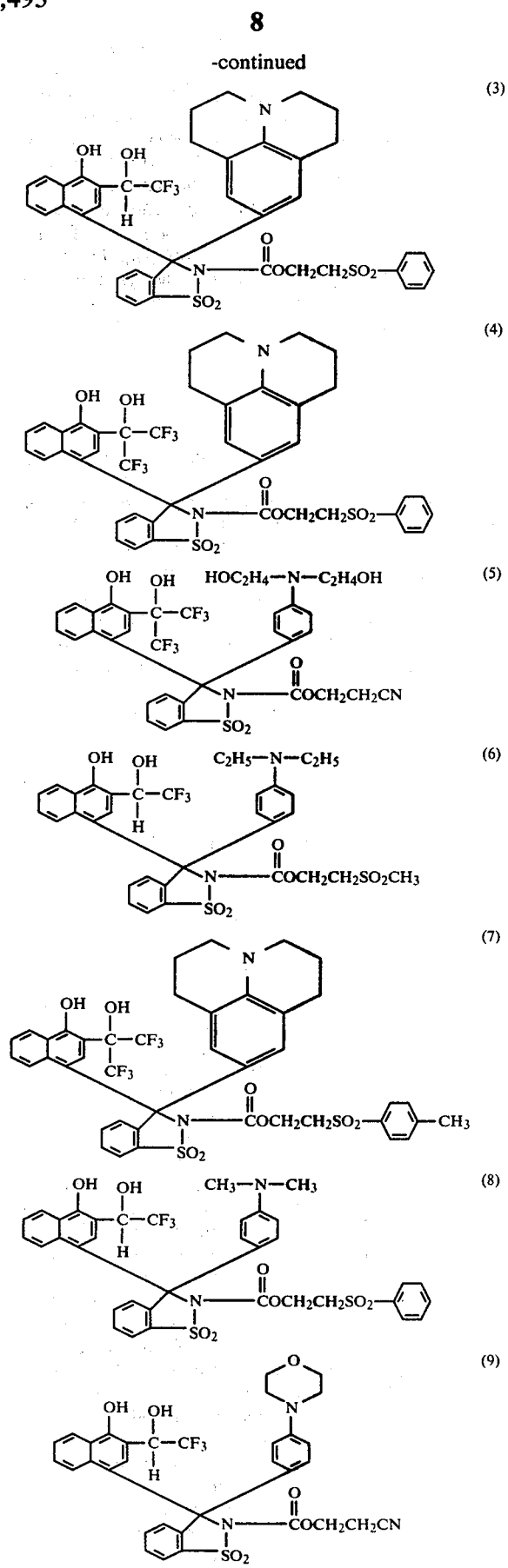

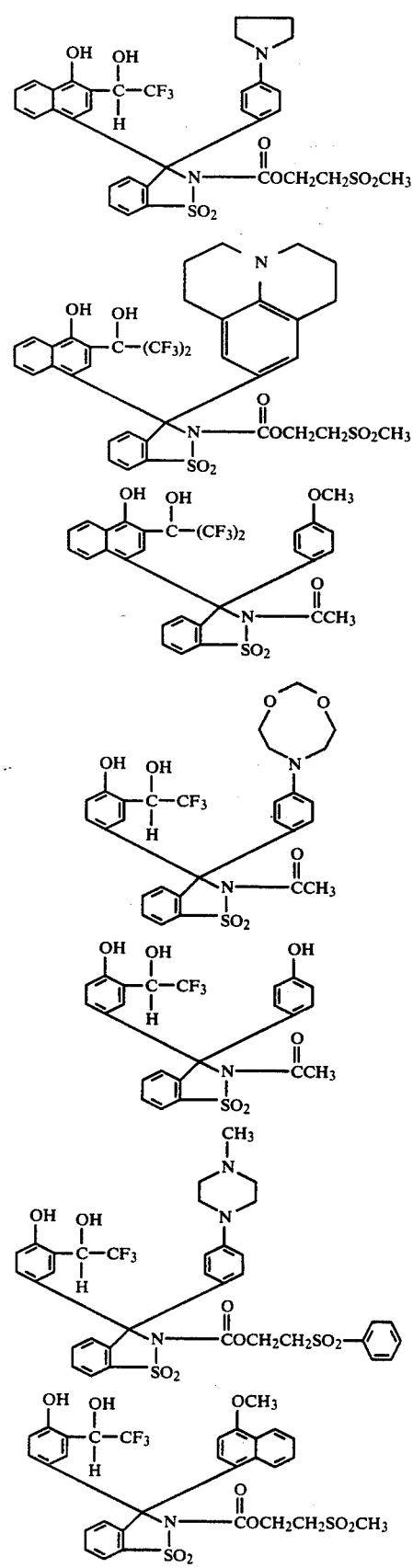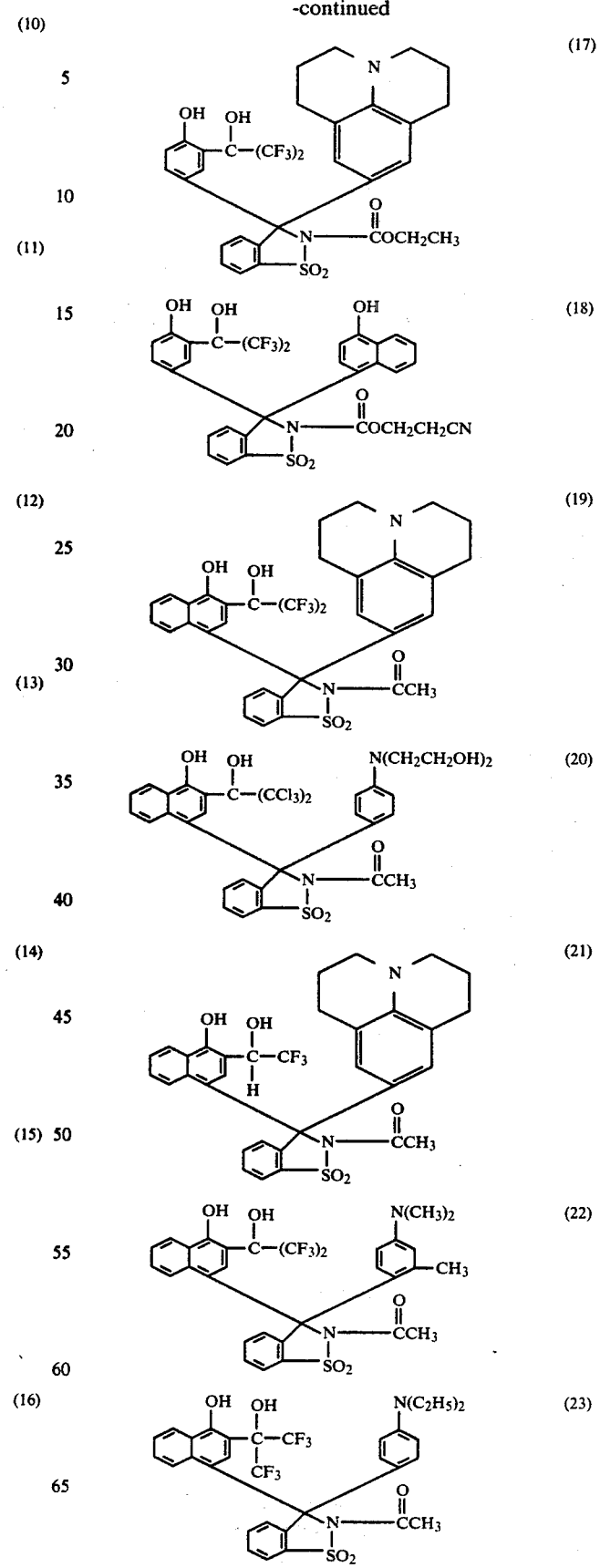

-continued

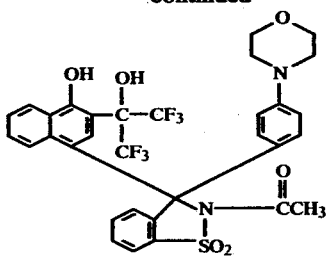
(24)

One method of synthesizing the compounds of the present invention comprises reacting (a) a carbocyclic aryllithium compound selected from a 4-OLi-naphthyllithium compound substituted in the 3-position with a group,

wherein $R^I$ is perhalomethyl and $R^{II}$ is hydrogen or perhalomethyl and a 4-OLi-phenyllithium compound substituted in the 3-position with a group,

wherein $R^I$ is perhalomethyl and $R^{II}$ is hydrogen or perhalomethyl and (b) a compound selected from a 3-substituted-benz[d]isothiazole-1,1-dioxide wherein said 3-substituent is a phenyl moiety or a naphthyl moiety provided said 3-substituent is a phenyl moiety when said carbocyclic aryllithium compound is said 4-OLi-naphthyllithium compound and a 3-substituted-naphtho[1,8-de]-1,2-thiazine-1,1-dioxide wherein said 3-substituent is a phenyl moiety or a naphthyl moiety provided said 3-substituent is a phenyl moiety when said carbocyclic aryllithium compound is said 4-OLi-naphthyllithium compound to give (c) a 3,3-disubstituted-2,3-dihydrobenz[d]isothiazole-1,1-dioxide or a 3,3-disubstituted-2,3-dihydronaphtho[1,8-de]-1,2-thiazine-1,1-dioxide wherein one of the 3,3 substituents is a 4'-OH-1'-naphthyl moiety substituted in the 3'-position with

wherein $R^I$ and $R^{II}$ have the same meaning given above or a 4'-OH-1'-phenyl moiety substituted in the 3'-position with

wherein $R^I$ and $R^{II}$ have the same meaning given above and the other of the 3,3-substituents is a phenyl moiety or a naphthyl moiety.

The 3-substituted-benz[d]isothiazole-1,1-dioxides reacted with the "lithiated" phenol (or 1-naphthol) reagent may be a 3-(4'-OP-1'-phenyl/4'-OP-1'-naphthyl)-benz[d]isothiazole-1,1-dioxide or a 3-(phenyl/naphthyl)benz[d]isothiazole-1,1-dioxide wherein the 3-(phenyl/naphthyl) substituent may be unsubstituted or substituted with other than a 4'-OP substituent. It will be understood that the corresponding 3-substituted naphtho[1,8-de]-1,2-thiazine-1,1-dioxides also may be reacted with the "lithiated" reagent.

When 3-(4'-OP-1'-phenyl/4'-OP-1'-naphthyl)-benz[d]isothiazole-1,1-dioxides are employed as starting materials in this method, they are prepared by blocking the functional hydroxy group and any substituent group(s), as may be appropriate, of the selected 4-halophenol or 4-halo-1-naphthol and converting the blocked phenol or 1-naphthol to the corresponding Grignard or lithium reagent which is then reacted with a saccharin reagent. The 4-halo substituent may be chloro, bromo or iodo when the lithium reagent is prepared by reacting the blocked phenol or blocked 1-naphthol with lithium metal and is either bromo or iodo when the lithium reagent is made via a lithium exchange reaction using, for example, n-butyllithium. In preparing the Grignard reagent by reacting the blocked phenol or 1-naphthol with magnesium metal, the 4-halo substituent may be chloro, bromo or iodo. The Grignard or lithium reagent thus prepared is then reacted with saccharin, the N-lithium salt of saccharin or saccharin pseudo-chloride to yield the corresponding 3-(4'-OP-1'-phenyl/4'-OP-1'-naphthyl)benz[d]isothiazole-1,1-dioxide. Generally, the Grignard reagent is reacted with the pseudo-chloride, and the lithium reagent is reacted with the N-lithium salt. The 3-(4'-OP-1'-phenyl/4'-OP-1'-naphthyl)naphtho[1,8-de]-1,2-thiazine-1,1-dioxides may be prepared in a similar manner by reacting the Grignard or lithium reagent with 2,3-dihydro-3-oxo-naphtho[1,8-de]-1,2-thiazine-1,1-dioxide, its pseudo-chloride or the N-lithium derivative thereof.

The groups selected for protecting the functional phenolic or naphtholic hydroxy group and other hydroxy groups that may be present in the phenol or 1-naphthol should be stable to and compatible with organolithium and Grignard reagents and should protect the hydroxy group(s) against reaction under the conditions encountered in preparing the starting materials. It will be appreciated that starting materials without protecting groups on the 3-(4'-OH-1'-phenyl/4'-OH-1'-naphthyl) moiety may be employed in the subsequent acylation reactions. However, it is more convenient to leave the protecting group(s) on the starting materials derived from the 3-(4'-OP-1'-phenyl/4'-OP-1'-naphthyl)benz[d]isothiazole-1,1-dioxides and remove the protecting groups subsequent to the acylation reaction. Thus, the protecting group selected should be capable of being easily removed under weakly acid conditions to regenerate the hydroxy group(s) without the removal of or adversely affecting the N-substituent or other substituents that may be present. Alkyl groups, such as methyl and ethyl, may be employed in those instances where they can be removed without removal of the N-substituent. Because they can be readily removed without disturbing the N-substituent or other substituents, the phenol or 1-naphthol preferably is protected with methoxymethyl, 2'-tetrahydropyranyl or dimethyl-t-butylsilyl. The blocked phenols and 1-naphthols employing these protecting groups may be prepared by methoxymethylation as described, for example, by Kaoru Fuji et al, *Synthesis*, 4, pp. 276–277 (1975), by tetrahydropyranylation as described, for example, by William E. Parham et al, *J. Amer. Chem. Soc.*, 70, pp. 4187–4189 (1948) or by silylating with dimethyl-t-butylsilyl chloride in the presence of imidazole as described by E. J. Corey et al, *J. Amer. Chem. Soc.*, 94, pp. 6190–6191 (1972).

When the starting materials are 3-(phenyl/naphthyl)-benz[d]isothiazole-1,1-dioxides, i.e., other than 3-(phenyl/naphthyl) compounds containing a 4'-OP substituent, they may be prepared in a similar manner by blocking hydroxy and/or other substituent group(s), as may be appropriate, of the selected halo-benzene or halo-naphthalene compound and converting the halo compound to the corresponding Grignard or lithium reagent which is then reacted with the saccharin reagent to give the corresponding 3-substituted-benz[d]isothiazole-1,1-dioxide.

Certain 3-(4'-OP-1'-phenyl/4'-OP-1'-naphthyl)benz-[d]isothiazole-1,1-dioxides form the subject matter of copending U.S. Patent application Ser. No. 836,024 now No. 4,181,660 of Alan L. Borror, L. Cincotta, E. W. Ellis, J. W. Foley and M. M. Kampe filed Sept. 23, 1977. 3-(Phenyl/naphthyl)-benz[d]isothiazole-1,1-dioxides substituted with certain N-heterocyclic moieties form the subject matter of copending U.S. Patent application Ser. No. 836,022 now No. 4,139,704 of Alan L. Borror, J. W. Foley and J. W. Lee, Jr. filed Sept. 23, 1977, and 3-(9'-julolidinyl)benz[d]isothiazole-1,1-dioxide forms the subject matter of copending U.S. Patent application Ser. No. 836,023 now No. 4,140,689 also filed Sept. 23, 1977.

The "lithiated" derivative of the perhalomethylcarbinol-substituted phenol or 1-naphthol is prepared by reacting the selected 4-halophenol or 4-halo-1-naphthol with at least three molar equivalents of lithium metal or preferably n-butyllithium as illustrated below

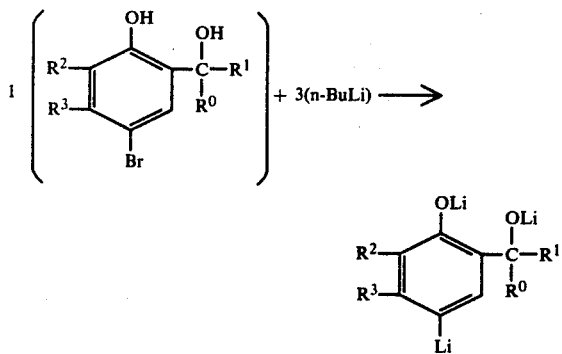

The perhalomethylcarbinol-substituted phenols and 1-naphthols may be prepared according to the procedures set forth by Basil S. Farah et al, *J. Org. Chem.*, Vol. 30, p. 1003 (1965) and are halogenated in any conventional manner to give the 4-halo derivatives, for example, by reacting the perhalomethylcarbinol-substituted compound with chloride or bromine, with or without a catalyst; N-bromosuccinimide or iodinemonochloride.

In carrying out the synthesis, the selected 3-substituted-benz[d]isothiazole-1,1-dioxide is reacted with at least one molar equivalent of the "lithiated" phenol or 1-naphthol in an inert organic solvent, such as, benzene, diethyl ether, dioxane, hexane, toluene, petroleum ether or tetrahydrofuran. The reactants may be employed in equivalent, i.e., equimolar amounts but ordinarily an excess of about 0.1 to 1.0 mole of the "lithiated" phenol or 1-naphthol is employed per 1.0 mole of the 3-substituted-benz[d]isothiazole-1,1-dioxide. The reaction temperature may vary over a relatively wide range from about −80° to 50° C. as may be readily determined for the particular reactants. For achieving maximum yields, the reaction generaly is conducted at a temperature below about 0° C. and preferably between about −65° C. and −25° C. As a matter of convenience, the 4-halo perhalomethylcarbinol-substituted phenol or 1-naphthol is reacted with the requisite amount of n-butyllithium at reduced temperatures of about −50° to −70° C. in an inert organic solvent such as those enumerated above to give the corresponding "lithiated" derivative and then the 3-substituted-benz[d]isothiazole-1,1-dioxide is added without isolating the "lithiated" derivative.

To prepare the

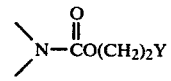

compounds, the selected 3,3-disubstituted-2,3-dihydrobenz[d]isothiazole-1,1-dioxide as prepared above is reacted with at least one molar equivalent of an acid halide of the formula

wherein W is chloro or bromo and Y is hydrogen or an electron-withdrawing group in pyridine solution to give the corresponding

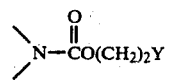

compound. About 1 to 6 moles of acid halide may be used for each mole of the 3,3-disubstituted-2,3-dihydrobenz-[d]isothiazole-1,1-dioxide, and usually 5 to 6 moles are employed. Since the reaction is exothermic, external heating is initially unnecessary, but the reaction mixture may be heated to facilitate completion of the reaction, if desired. Ordinarily, the reaction temperature ranges between about 0° and 100° C., and, if desired, the reaction may be conducted in an inert atmosphere, for example, under nitrogen. Preferably, the acylation reaction is conducted in the presence of acidic alumina or a zeolite molecular sieve. The amount of acidic alumina and molecular sieve may be readily determined empirically, and ordinarily, about 2 to 20 g of the alumina or molecular sieve per gram of 3,3-disubstituted-2,3-dihydrobenz[d]isothiazole-1,1-dioxide is sufficient to give the desired

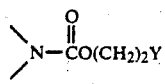

compound as the major or exclusive reaction product, i.e., with little or no derivatization of the hydroxy groups.

The carboxylic acid halies may be prepared by reacting the selected HO(CH₂)₂Y with phosgene to give the corresponding

It will be appreciated that any protecting group, P, as may be present are removed subsequent to the acylation step by treating the N-acylated compound with acid having a pH between about 0.1 and 5.0 at a temperature between about 20° and 100° C. The acid may be an inorganic acid, such as, hydrochloric acid or sulfuric acid in a protic solvent, e.g., water, alkanol, such as, methanol or ethanol, or aqueous alkanol, or the acid may be an organic acid, such as, acetic acid or trifluoroacetic acid alone or in a protic solvent, such as those mentioned above.

To prepare the

compounds, the selected 3,3-disubstituted-2,3-dihydrobenz[d]isothiazole-1,1-dioxide as prepared above is reacted with at least three molar equivalents of an acid halide of the formula

wherein W is chloro or bromo and R has the same meaning given above in pyridine solution to give a triacylated intermediate. About 3 to 6 moles of acid halide may be used for each mole of the 3,3-disubstituted-2,3-dihydrobenz[d]isothiazole-1,1-dioxide depending upon the number of unblocked —OH groups present in addition to the >NH of the isothiazole ring, and usually 5 to 6 moles are employed. Since the reaction is exothermic, external heating may be unnecessary, but the reaction mixture may be heated to facilitate completion of the reaction, if desired. Ordinarily, the reaction temperature ranges between about 0° and 100° C., and if desired, the reaction may be conducted in an inert atmosphere, for example, under nitrogen.

The carboxylic acid halides may be prepared in a conventional manner, for example, by reacting the selected carboxylic acid, RCOOH, with phosphorus trichloride phosphorus pentachloride or thionyl chloride to give the corresponding RCOCl.

The acyl groups,

are removed from the 4'-hydroxy and carbinol hydroxy groups of the acylated 3-(4'-hydroxy-3'-perhalomethylcarbinol-1'-phenyl/4'-hydroxy-3'-perhalomethylcarbinol-1'-naphthyl) substituent of the sulfam(na)phthalein by treating with 0.01 to 2.0 N base at a temperature between about 0° and 40° C., and usually room temperature. The base may be, for example, methylamine but preferably is an ionic hydroxide base, such as, tetrabutylammonium hydroxide, sodium hydroxide or potassium hydroxide in a solvent, such as, water and/or a lower alkanol, e.g., methanol or ethanol.

As in the previous acylation reaction, any protecting groups, P, as may be present in the other 3-substituent of the sulfam(na)phthalein are removed by treating the N-acylated compound with acid having a pH between about 0.1 and 5.0 at a temperature between about 20° and 100° C. The acid may be an inorganic acid, such as, hydrochloric acid or sulfuric acid in a protic solvent, e.g., water, alkanol, such as, methanol or ethanol, or aqueous alkanol, or the acid may be an organic acid, such as, acetic acid or trifluoroacetic acid alone or in a protic solvent, such as those mentioned above.

The method of reacting the "lithiated" perhalomethylcarbinol-substituted phenol or 1-naphthol and the 3-(substituted)benz[d]isothiazole-1,1-dioxide to give the 3,3-disubstituted intermediate forms the subject matter of copending U.S. Patent application Ser. No. 956,908 of Louis Cincotta and James W. Foley filed concurrently herewith. The method of reacting the aforementioned 3,3-disubstituted-2,3-dihydrobenz[d]isothiazole-1,1-dioxide intermediates with

to give the corresponding

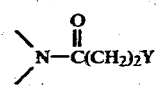

compounds forms the subject matter of copending U.S. Patent application Ser. No. 957,162, now No. 4,210,752 of Louis Cincotta and James W. Foley and the method of reacting the aforementioned 3,3-disubstituted-2,3-dihydrobenz[d]isothiazole-1,1-dioxide intermediates with

to give the triacylated compound followed by selectively removing the

groups from the hydroxy groups to give the

products forms the subject matter of copending U.S. Patent application Ser. No. 956,907 of Louis Cincotta and James W. Foley both filed concurrently herewith. For convenience, the specifications of aforementioned applications Ser. Nos. 956,908; 957,162; now Nos.

4,210,752 and 956,907 are specifically incorporated herein.

The compounds of the present invention also may be prepared according to the method disclosed and claimed in copending U.S. Patent application Ser. No. 836,010 of Stanley M. Bloom, Alan L. Borror and James W. Foley filed Sept. 23, 1977, by reacting a 3,3-disubstituted-2,3-dihydrobenz[d]isothiazole-1,1-dioxide wherein one of the 3-substituents is (4'-OP-1'-phenyl/4'-OP-1'-naphthyl) possessing

in the 3'-position and a carboxylic acid halide, such as,

to give the corresponding N-carbonyl derivative followed by removing the protecting group(s), P, with dilute acid to yield the product compounds. The 3,3-disubstituted-2,3-dihydrobenz[d]isothiazole-1,1-dioxides employed in the foregoing method may be prepared by reacting a 3-(4'-OP-1'-phenyl/4'-OP-1'-naphthyl)benz[d]isothiazole-1,1-dioxide possessing

in the 3'-position and a phenyllithium or a naphthyllithium reagent as disclosed and claimed in copending U.S. Patent application Ser. No. 836,008 of Alan L. Borror, Louis Cincotta, James W. Foley and Marcis M. Kampe filed Sept. 23, 1977, or by reacting a 3-(phenyl/naphthyl)benz[d]isothiazole-1,1-dioxide and a 4'-OP-phenyllithium/4'-OP-naphthyllithium compound possessing

in the 3'-position to give the corresponding 3,3-disubstituted-2,3-dihydrobenz[d]isothiazole-1,1-dioxide as disclosed and claimed in copending U.S. Patent application Ser. No. 836,025 now No. 4,178,447 of Alan L. Borror, James W. Foley, Marcis M. Kampe and John W. Lee, Jr., also filed Sept. 23, 1977. The protecting groups, P, may be those enumerated above, but preferably, in blocking the perhalomethylcarbinol-substituted phenols and 1-naphthols, alkyl groups, such as, benzyl are employed. The 3-substituted-benz[d]isothiazole-1,1-dioxides employed as starting materials in aforementioned applications Ser. Nos. 836,008 and 836,025 now No. 4,178,447 are prepared as described above.

The following examples are given to further illustrate the present invention and are not intended to limit the scope thereof.

EXAMPLE 1

Preparation of the compound having the formula

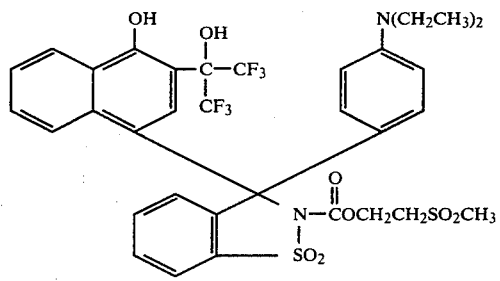

(a) 4-Bromo-2-(α-hydroxy-α-trifluoromethyl-β,β,β-trifluoroethyl)-1-naphthol (1.0 g) was dissolved in 25 ml tetrahydrofuran at room temperature under nitrogen, then cooled to −65° C. To this solution was added dropwise 3.21 ml of butyllithium (2.4 M in hexane). The resulting solution was stirred for one hour at −65° C. and then 3-(4'-N,N-diethylamino-1'-phenyl)-benz[d]isothiazole-1,1-dioxide (0.51 g) was added, the solution warmed to −20° C., then cooled back to −65° C. and stirred for one hour. TLC on silica gel with ether showed that the reaction was complete. The reaction solution was poured into 200 ml of water, the pH adjusted to 6 with conc. HCl and the resulting solution extracted with ether. The ether layer was separated and washed with 200 ml of 1 N sodium hydroxide. The aqueous sodium hydroxide layer was separated, washed well with ether, then neutralized with conc. HCl and extracted with ether. The ether extract was dried over anhydrous sodium sulfate and evaporated to give 3-[(-3'-α-hydroxy-α-trifluoromethyl-β,β,β-trifluoroethyl)-4'-hydroxy-1'-naphthyl]-3-[4'-N,N-diethylamino-1'-phenyl]-2,3-dihydrobenz[d]isothiazole-1,1-dioxide as a green solid (0.82 g; 50% yield).

(b) The compound prepared in step (a) above (0.7 g) was dissolved in 25 ml pyridine at room temperature. To this was added 0.21 g of ClCOOCH$_2$CH$_2$SO$_2$CH$_3$ and the reaction mixture stirred for several hours. TLC on silica gel with ether indicated no apparent reaction. Thus, additional acid halide (0.42 g) was added and the mixture stirred overnight. The reaction mixture was poured into water, extracted with ether and the ether extract evaporated. The title compound was obtained as a blue compound from the ether residue by preparative TLC on silica gel.

The 3-(4'-N,N-diethylamino-1'-phenyl)benz[d]isothiazole-1,1-dioxide was prepared as follows 4-Bromo-N,N-diethylaniline (22.8 g) was dissolved in 100 ml. of anhydrous tetrahydrofuran under nitrogen and then cooled to −74° C. To this solution was added dropwise 41.8 ml of n-butyllithium (2.4 M in hexane) over a 50-minute period. (The temperature was maintained at −70° C. during the addition.) The solution was stirred for one hour. Then a solution of the N-lithium salt of saccharin in 100 ml of tetrahydrofuran was added dropwise to the aniline solution at −70° C. using a double ended needle. The resulting reaction mixture was stirred for 4 hours, poured slowly into 1 liter of water and the pH adjusted to 6 with conc. HCl. An orange precipitate formed which was filtered, dried and dissolved in 250 ml of methanol containing about 5 ml of conc. HCl. The solution was refluxed for 30 minutes and the precipitate collected to give 14.0 g of the tital compound (melting range 207°–208° C.).

EXAMPLE 2

Preparation of the compound having the formula

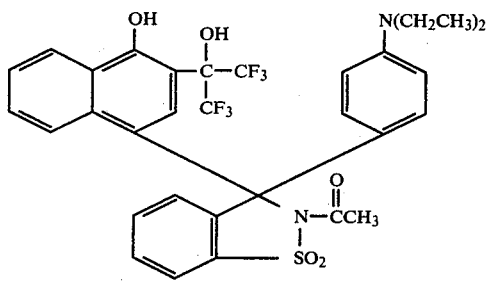

(a) 4-Bromo-2-(α-hydroxy-α-trifluoromethyl-β,β,β-trifluoroethyl)-1-naphthol (1.0 g) was dissolved in 20 ml of anhydrous tetrahydrofuran at room temperature. The solution was then cooled to −65° C., and 3.21 ml of n-butyllithium (2.4 M in hexane) was added dropwise (an exotherm occured during approximately 1 ml of the addition). The resulting light yellow solution was then stirred for one hour at −65° C. To the solution was added 0.81 g of 3-(4'-N,N-diethylamino-1'-phenyl)-benz[d]isothiazole-1,1-dioxide. The reaction solution was allowed to warm to −40° C. then poured into 200 ml of water, made pH 6 with conc. HCl and extracted with ether. The ether was then washed with 200 ml of 1 N sodium hydroxide. The sodium hydroxide solution was separated, washed with ether, then neutralized with HCl. The neutralized solution was extracted with ether, the ether dried over sodium sulfate and evaporated to leave a light green solid. Preparative TLC on silica gel with ether gave 0.5 g of 3-[(3'-α-hydroxy-α-trifluoromethyl-β,β,β-trifluoroethyl)-4'-hydroxy-1'-naphthyl]-3-[4'-N,N-diethylamino-1'-phenyl]-2,3-dihydrobenz[d]isothiazole-1,1-dioxide.

(b) The compound prepared in step (a) (0.5 g) was dissolved in 25 ml of pyridine and 2 ml of acetylchloride was added dropwise at room temperature. The reaction solution was stirred for 6 hours, poured into 500 ml of water, and the tan precipitate was filtered, washed well with water and vacuum dried.

(c) The triacetylated compound prepared in step (b) was dissolved in 100 ml of methanol and 5 drops of 50% aqueous sodium hydroxide solution was added. The resulting purple solution was stirred for 2 hours. TLC on silica gel with ether showed that de-acetylation of the —OH groups was complete. The methanol was removed under vacuum. After neutralization with HCl, chloroform was added to the residue and sodium sulfate for drying. The solution was filtered and the chloroform evaporated to leave 0.584 g of the title compound as a cyan solid.

EXAMPLE 3

Preparation of the compound having the formula

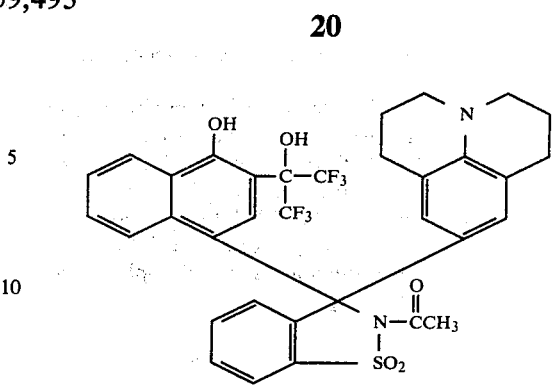

The title compound was prepared according to the procedure described in Example 2 above except that 4-bromo-2-(α-hydroxy-α-trifluoromethyl-β,β,β-trifluoroethyl)-1-naphthol and 3-(9'-julolidinyl)benz[d]isothiazole-1,1-dioxide were employed in step (a).

The 3-(9'-julolidinyl)benz[d]isothiazole-1,1-dioxide was prepared as follows:

(a) 134 g (0.758 mol) of 98% julolidine was dissolved in 500 ml of glacial acetic acid. To this solution was added a solution of 121 g (0.758 mol) of bromine in 2400 ml of glacial acetic acid. After the addition, the reaction mixture was stirred for 15 minutes and then tested for excess bromine using KI paper. More bromine was added until an excess was detected. The reaction mixture was then stirred for 1 hour at room temperature. The pink solid which formed was collected and washed several times with ether and dried in a vacuum oven overnight to give 245 g of the hydrobromide salt of 9-bromojulolidine. Yield 92% by weight.

(b) 75 g (0.22 mol) of 9-bromojulolidine hydrobromide prepared in step (a) was suspended in 1200 ml of ether. To the suspension was added 650 ml of 1 N sodium hydroxide and the mixture stirred for 5–10 minutes. The two layers were separated and the aqueous layer was extracted with 1000 ml of ether. The organic layers were combined, dried over anhydrous calcium sulfate and the ether evaporated to yield 51.97 g (0.206 mol) of 9-bromojulolidine as a dark oil.

(c) The 9-bromojulolidine was dissolved in 400 ml of dry tetrahydrofuran under nitrogen at −65° C. 85.8 ml of n-butyllithium (2.4 M in hexane) was added dropwise giving a tan slurry.

(d) 37.75 g (0.206 mol) of saccharin was dissolved in 400 ml of dry tetrahydrofuran under nitrogen at −65° C. 85.8 ml (0.206 mol) of n-butyllithium (2.4 M in hexane) was added dropwise until a permanent orange colored endpoint was reached. The mixture was stirred for 1 hour at −65° C. and then used directly in step (e).

(e) The mixture of step (d) was added to the tan slurry of step (c) at −60° C. to −50° C. through a double ended needle. After the addition was completed, the reaction mixture was stirred for 1 hour at −60° C. and gradually warmed to room temperature. The reaction mixture was then poured into 800 ml of water and the pH adjusted to 5–6 with conc. HCl. The orange precipitate which formed was collected to give 13.9 g of the title compound. The filtrate was extracted with ether, dried and evaporated to give 46 g of a dark oil. The oil was washed with hot hexane and then dissolved in hot ethanol (500 ml) and 75 drops of conc. HCl was added. The ethanol was cooled and 7.53 g of orange crystals were collected to give the title compound in a total yield of 21.47 g.

The compound of Example 3 also was prepared as follows:

(a) 4-Bromo-2-(α-benzyloxy-α-trifluoromethyl-β,β,β-trifluoroethyl)-benzylnaphthyl ether (1.5 g) was dissolved in 20 ml of tetrahydrofuran at room temperature under nitrogen and then cooled to −65° C. To this solution was added dropwise 1.7 ml of butyllithium (1.6 M in hexane) giving a yellow solution which was stirred for 15 minutes at −50° C. and then allowed to warm to −5° C. over about 15 minutes. 3-(9′-julolidinyl)benz[d]isothiazole-1,1-dioxide (0.6 g) was added portionwise (with each addition solution turned yellow then amber). This reaction solution was then stirred for 30 minutes at room temperature, poured into 200 ml of water, adjusted to pH 6, extracted with ether and the ether dried and evaporated to approximately 10 ml. This solution was placed on a silica gel column wet-packed in 1:1 hexane/ether and eluted. The proper fractions were collected and yielded upon evaporation 1.0 g (69% by weight) of 3-[4′-benzyloxy-3′-(α-benzyloxy-α-trifluoromethyl-β,β,β-trifluoroethyl)-1′-naphthyl]-3-(9′-julolidinyl)-2,3-dihydrobenz[d]isothiazole-1,1-dioxide.

(b) The compound prepared in step (a) (0.5 g) was dissolved in 15 ml of anhydrous pyridine. To this solution was added 0.5 ml of acetyl chloride. (An exotherm and the precipitation of a white solid was observed.) The resulting mixture was stirred at room temperature for 16 hours. During the first hour solution occurred and then the solution became darker with time turning to a pink-red color. The solution was poured into 200 ml of water. A pinch of sodium chloride was added, and a precipitate formed. The tan precipitate was recovered by filtration, washed with water and dried. The precipitate was dissolved in methylene chloride, and preparative TLC on silica gel with 8/10 hexane/ether gave a pink spot which was removed with acetone. The acetone was evaporated to give the title compound.

4-Bromo-2-(α-benzyloxy-α-trifluoromethyl-β,β,β-trifluoroethyl)-benzylnaphthyl ether was prepared as follows:

4-Bromo-2-(α-hydroxy-α-trifluoromethyl-β,β,β-trifluoroethyl)-1-naphthol and 12 ml of benzyl bromide were added to 100 ml of N,N-dimethylformamide under nitrogen. To this solution was added 5.0 g of 50% sodium hydride oil dispersion in two portions. After adding the first half, an exotherm was observed with the temperature rising to about 40° C. with $H_2$ evolution. The solution was stirred for 5 minutes and then the second half was added. Another vigorous evolution of hydrogen occurred and a second exotherm occurred to about 48° C. After 5 minutes at 48° C., the temperature began to drop. The color of the reaction went from light yellow to green to cyan. This was stirred overnight and the resulting solution (now light yellow-green) was slowly poured into 400 ml of 1 N sodium hydroxide, extracted and evaporated to leave a green oil which was vacuum dried at 100° C. The residue was then heated in 400 ml of hexane and cooled. A green oil precipitated. The solution was decanted through a Celite pod to give a strawcolored solution which was concentrated to give a yellow oil. 100 Ml of ethanol was added and the solution heated to reflux. This was cooled and allowed to stand at room temperature overnight giving 11 g of white crystals (melting range 109°–110° C.). TLC on silica gel with hexane showed one spot.

EXAMPLE 4

Preparation of the compound having the formula

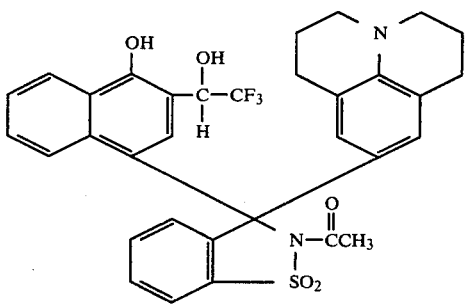

The title compound was prepared according to the procedure described in Example 2 above except that 4-bromo-2-(α-hydroxy-β,β,β-trifluoroethyl)-1-naphthol and 3-(9′-julolidinyl)benz[d]isothiazole-1,1-dioxide were employed in step (a).

EXAMPLE 5

Preparation of the compound having the formula

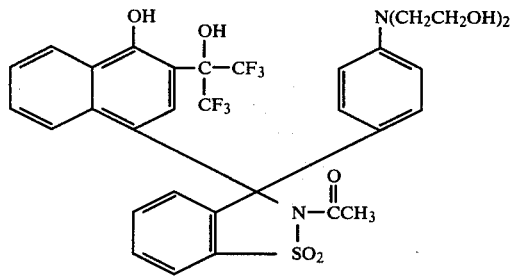

The title compound was prepared according to the procedure described in Example 2 above except that 4-bromo-2-(α-hydroxy-α-trifluoromethyl-β,β,β-trifluoroethyl)-1-naphthol and 3-[4′-N,N-di(β-2″-tetrahydropyranyloxyethyl)-1′-phenyl]benz[d]isothiazole-1,1-dioxide were employed in step (a) and the tetrahydropyranol protecting groups were removed subsequent to de-acetylation of the hydroxy groups by refluxing in methanol made acidic with conc. HCl for about one hour.

The 3-[4′-N,N-di(β-2″-tetrahydropyranyloxyethyl)-1′-phenyl]benz[d]isothiazole-1,1-dioxide was prepared as follows:

4-Bromo-N,N-di(β-2′-tetrahydropyranyloxyethyl)-aniline (10.0 g) was dissolved in 100 ml of tetrahydrofuran. The solution was cooled to −65° C. and 10 ml of n-butyllithium (2.4 M in hexane) was added dropwise under nitrogen at a rate to maintain the temperature below −65° C.

In a separate flask, saccharin (4.28 g) was dissolved in 50 ml of tetrahydrofuran under nitrogen, and the solution was cooled to −65° C. n-Butyllithium (2.4 M in hexane) was added until a peach color persisted (about 9.0 ml).

The latter solution of the N-lithium salt of saccharin was added to the aniline solution by hollow wire over a 10 minute period. (Initially a green color formed which changed to tan.) The reaction mixture was stirred for 1.5 hours and poured into 2 liters of water. The pH was adjusted to 6 with conc. HCl, and the mixture extracted with ether. The ether extract was dried and evaporated and the residue was dissolved in 100 ml of toluene. Two spatula tips of toluene sulfonic acid monohydrate were added, and the solution was refluxed for about 6 hours. The toluene was evaporated and the residue was dissolved in 2 liters of ether. The ether solution was cooled and the crystalline solid was collected to give 4.0 g of the title compound (melting range 100°–101° C.).

Tetrahydropyranylation of p-Br-N,N-di(β-hydroxyethyl)aniline was carried out as follows:

p-Br-N,N-di(β-hydroxyethyl)aniline (20.0 g) was dissolved in 475 ml of dichloromethane containing 60 ml of dihydropyran. To this solution was added 1 ml of conc. HCl, and the reaction solution was stirred for about 5.5 hours. The solution was then washed with water containing enough sodium hydroxide to neutralize any acid present. The dichloromethane was separated, dried over anhydrous sodium sulfate and evaporated under reduced pressure with a steam bath (aspirator) leaving an oil. The oil was heated to 115° C. at 0.1 mm Hg to distill off impurities leaving 33.0 g of the title compound.

EXAMPLE 6

Preparation of the compound having the formula

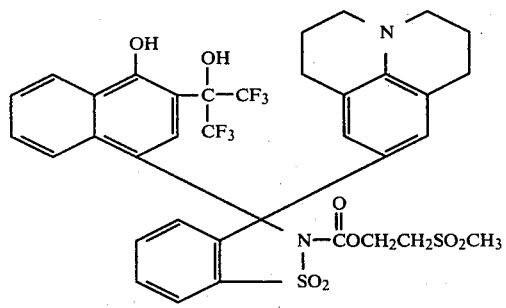

(a) 3-[(3'-α-hydroxy-α-trifluoromethyl-β,β,β-trifluoroethyl)-4'-hydroxy-1'-naphthyl]-3-(9'-julolidinyl)-2,3-dihydrobenz[d]isothiazole-1,1-dioxide was prepared according to the procedure given in Example 2 above except that 4-bromo-2-(α-hydroxy-α-trifluoromethyl-β,β,β-trifluoroethyl)-1-naphthol and 3-(9'-julolidinyl)-benz[d]isothiazole-1,1-dioxide were employed in step (a).

(b) The compound prepared in step (a) (17.0 g) was dissolved in 400 ml of pyridine at room temperature under nitrogen. To this solution was added ½ pound of Type 3A molecular sieves. This was stirred mechanically in the dark and 30 g of β-(methylsulfonyl)ethylchloroformate was added and stirred for 3 hours. TLC on silica gel with 1:9 methanol/ether showed a trace of the starting isothiazole. The reaction mixture was filtered, washed with methylene chloride, poured into 5 liters of water and extracted with 1500 ml of methylene chloride. The methylene chloride was dried over sodium sulfate and evaporated under reduced pressure to remove all of the pyridine. The residue was washed with hexane several times and then vacuum dried to give 21.0 g of the title compound as a blue solid.

EXAMPLE 7

Preparation of the compound of the formula

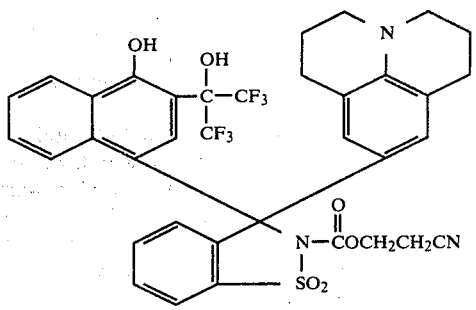

(a) 3-[(3'-α-hydroxy-α-trifluoromethyl-β,β,β-trifluoroethyl)-4'-hydroxy-1'-naphthyl]-3-(9'-julolidinyl)-2,3-dihydrobenz[d]isothiazole-1,1-dioxide was prepared according to the procedure given in Example 2 above except that 4-bromo-(3-α-hydroxy-α-trifluoromethyl-β,β,β-trifluoroethyl)-1-naphthol and 3-(9'-julolidinyl)-benz[d]isothiazole-1,1-dioxide were employed in step (a).

(b) The compound prepared in step (a) (1.5 g) was dissolved in 25 ml of pyridine; 3 g of acidic alumina was added; and then 1.0 ml of β-cyanoethylchloroformate was added. The resulting reaction mixture was stirred for 16 hours at room temperature. The yellow solution turned green to cyan. The alumina was removed from the pyridine by filtration. The filtrate was poured into 200 ml of water, extracted with ether and the ether dried over sodium sulfate and evaporated. The residue was purified by medium pressure column chromatography using a silica gel stationary phase and 5% methanol in methylene chloride as elutant. TLC of samples on silica gel with ether showed the title compound as a fairly pure product.

EXAMPLE 8

Preparation of the compound having the formula

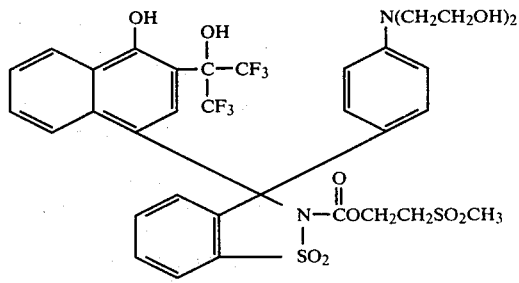

(a) 3-[3'-α-hydroxy-α-trifluoromethyl-β,β,β-trifluoroethyl-4'-hydroxy-1'-naphthyl]-3-[4'-N,N-di(β-2''-tetrahydropyranyloxyethyl)-1'-phenyl)benz[d]isothiazole-1,1-dioxide was prepared according to the procedure given in Example 2 above except that 4-bromo-2-(α-hydroxy-α-trifluoromethyl-β,β,β-trifluoroethyl)-1-naphthol and 3-[4'-N,N-di(β-2''-tetrahydropyranyloxyethyl)-1'-phenyl]benz[d]isothiazole-1,1-dioxide were employed in step (a).

(b) The compound prepared in step (a) (2.0 g) was dissolved in approximately 30 ml of pyridine. To this solution was added 20.0 g of Type 3A molecular sieves and 1.13 g of (β-methylsulfonyl)ethylchloroformate and then the reaction mixture was stirred vigorously at room temperature for 3 to 4 hours. TLC on silica gel using 80:20 hexane/acetone showed that a comparatively large amount of starting isothiazole was present. More (β-methylsulfonyl)ethylchloroformate (0.6 g) was added, and the mixture was stirred at room temperature overnight. The following morning only a trace of the starting isothiazole could be detected. The reaction mixture was poured into cold water overlayered with ethyl acetate. The ethyl acetate was decanted, washed with several portions of fresh water, dried over anhydrous sodium sulfate and the solvent removed leaving a dark blue, tacky residue. The residue was dried under vacuum in the presence of phosphorus pentoxide to yield 1.9 g of a dark blue solid.

The tetrahydropyranyl groups were removed by dissolving the blue solid in methanol, made acidic with conc. hydrochloric acid and refluxing for 1 hour. The methanol was removed by evaporation to yield the title compound.

4-Bromo-2-(α-hydroxy-α-trifluoromethyl-β,β,β-trifluoroethyl)-1-naphthol was prepared by adding a suspension of 50 g (0.161 mole) of 2-(α-hydroxy-α-trifluoromethyl)-1-naphthol in 500 ml of CCl₄ to a 3-necked, 2-liter flask equipped with a mechanical stirrer. This suspension was stirred while a solution of 8.5 ml (0.161 mole) Br₂ in 200 ml CCl₄ was added dropwise. Upon completion of the addition, the mixture was stirred for 2 hours, then filtered, and the filtrate evaporated under reduced pressure to leave a tan solid. This solid was dissolved with heating on a steam bath into 300 ml of ligroin (b.p. 90°–110° C.). 10 Grams of norit was added, heating was continued for a further 10 minutes, and then the mixture was filtered through a sintered glass funnel containing a celite pad. Upon cooling and filtration, 50 g of white crystals were collected (melting range 116°–117° C.). The mother liquor was concentrated to one-half the original volume and a second crop of 5 g (melting range 112°–115° C.) was collected to give a total yield of 55 g (88%).

EXAMPLE 9

Preparation of the compound having the formula

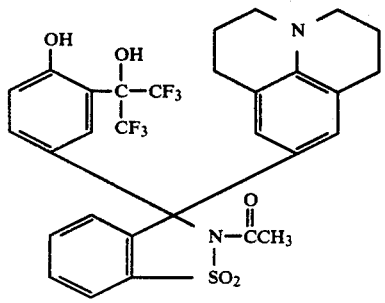

The title compound was prepared according to the procedure given in Example 2 above except that 4-bromo-2-(α-hydroxy-α-trifluoromethyl-β,β,β-trifluoroethyl)-1-phenol and 3-(9'-julolidinyl)benz[d]isothiazole-1,1-dioxide were employed in step (a).

EXAMPLE 10

Preparation of the compound having the formula

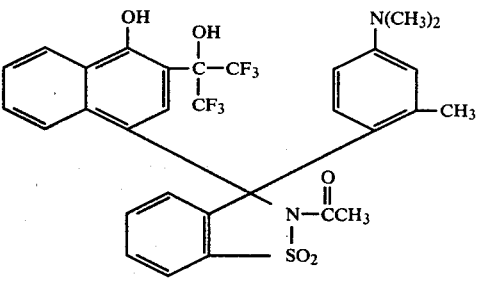

The title compound was prepared according to the procedure given in Example 2 above except that 4-bromo-2-(α-hydroxy-α-trifluoromethyl-β,β,β-trifluoroethyl)-1-naphthol and 3-(4'-N,N-dimethylamino-2'-methyl-1'-phenyl)benz[d]isothiazole-1,1-dioxide were employed in step (a).

EXAMPLE 11

Preparation of the compound having the formula

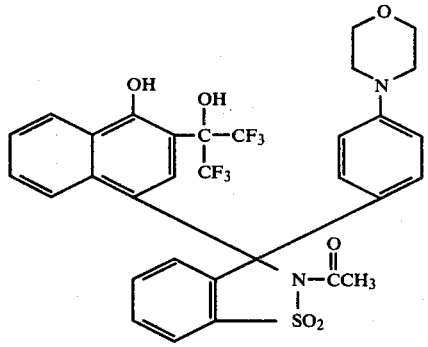

The title compound was prepared according to the procedure given in Example 2 above except that 4-bromo-2-(α-hydroxy-α-trifluoromethyl-β,β,β-trifluoroethyl)-1-naphthol and 3-(4'-N,N-dimethylamino-2'-methyl-1'-phenyl)benz[d]isothiazole-1,1-dioxide were employed in step (a).

EXAMPLE 12

Preparation of the compound having the formula

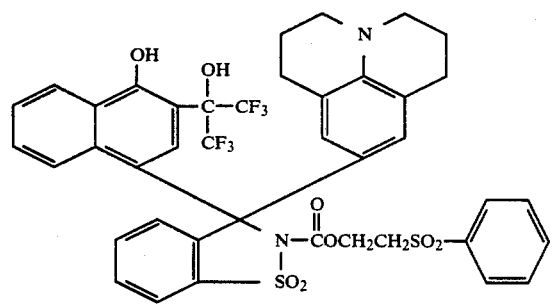

The title compound was prepared according to the procedure given in Example 6 using

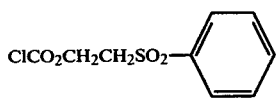

in (b).

Where it is desired to prepare sulfamnaphthaleins, it will be appreciated that 2,3-dihydro-3-oxo-naphtho[1,8-de]-1,2-thiazine-1,1-dioxide or its pseudo-chloride may be substituted for the saccharin reagents used in the foregoing Examples to give the corresponding sulfamnaphthalein intermediates and products. The pseudo-chloride may be prepared from the 3-oxo thiazine by reaction with $PCl_5$ as described above for the preparation of saccharin pseudo-chloride.

The compounds of the present invention wherein the Z substituent on the N atom of the ring-closing moiety is

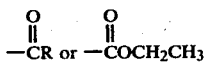

are useful as pH-sensitive indicator dyes and have reversibly alterable spectral absorption characteristics in response to changes in environmental pH. Besides their use in titrations and other analytical procedures where pH-sensitive indicator dyes are commonly employed, the compounds having a colorless form below a given pH may be used for providing colored optical filter agents in photographic products and processes where the pH is reduced subsequent to processing as described in U.S. Pat. No. 3,647,437 issued Mar. 7, 1972 to Edwin H. Land. This patent is concerned with diffusion transfer processes wherein the resulting photograph comprises the developed photosensitive layer(s) retained with the image-receiving layer as part of a permanent laminate. In the processes disclosed, a photographic film unit comprising a photosensitive element is developed in ambient light but further undesired exposure during processing is prevented by a light-absorbing material or optical filter agent which is retained in the processed film unit. In a preferred embodiment, the optical filter agent is a pH-sensitive dye, i.e., a dye possessing spectral absorption characteristics that are reversibly alterable in response to changes in environmental pH and particularly, a pH-sensitive dye having a colored or light-absorbing form above a given alkaline pH and a colorless or non-light-absorbing form below said pH. Though the pH-sensitive dye is usually included in the processing composition, it may be initially positioned in the film unit, for example, in a layer over the photosensitive element provided it is in its colorless form if photoexposure is to be effected through that layer. Upon application of an alkaline processing composition, the pH-sensitive dye is converted to its colored form, and after the desired processing time, it is converted back to its colorless form by reducing the environmental pH, e.g., by including an acid-reacting layer as part of the film unit. Where these compounds are initially colored and are converted from one to another color in response to changes in pH, they also may be employed for providing a colored optical filter agent or as photographic light-screening dyes, such as, antihalo or filter dyes, for example, in photographic processes where they are removed subsequent to processing.

Where the N-substituent is

and Y is an electron-withdrawing group, the compounds have a colored form in aqueous alkaline solution above a given alkaline pH and are discharged, e.g., decolorized independently of pH reduction by irreversible cleavage of the N-substituent after remaining in contact with said alkaline solution for a predetermined time. For example, the colored form generated from these compounds possessing a

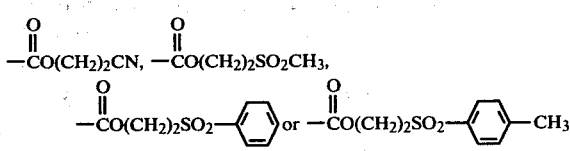

substituent on the N atom of the benz[d]isothiazole-1,1-dioxide moiety usually have a half-life (T ½) in approximately 1 N NaOH of less than 30 seconds. By T ½ is meant the time measured for one-half of the colored form to decolorize. When these compounds are initially colorless, they may be employed as colorless precursors for providing colored photographic optical filter agents for protecting an imagewise exposed photosensitive material from further exposure during processing in light as described in copending U.S. patent application Ser. No. 836,006 now U.S. Pat. No. 4,139,381 of Stanley M. Bloom, Alan L. Borror and James W. Foley filed Sept. 23, 1977. In the processes disclosed, the colorless filter agent precursor is initially disposed in a layer of the film unit, for example, in a layer coated over the photosensitive element, and subsequent to imagewise exposure of the photosensitive element, the colored optical filter agent is generated by contacting the colorless precursor with base, e.g., an aqueous alkaline processing composition. After remaining in contact with said base for a given time, the colored optical filter agent is discharged by forming a new compound which is substantially colorless and which is different from and non-reversible by a pH change to either said optical filter agent or said precursor. When these compounds are initially colored, they may be employed as light-screening dyes in photographic products and processes, i.e., as antihalation dyes positioned, for example, between a photosensitive silver halide layer and the film base or support or as filter dyes, for example, in multilayer, multicolor photographic materials to adjust the sensitometry for achieving the desired color balance. The use of these compounds as light-screening dyes in photographic products and processes is disclosed and claimed in copending U.S. patent application Ser. No. 957,161 now U.S. Pat. No. 4,186,001 of James W. Foley filed concurrently herewith. As discussed therein, a photographic film unit comprising a photosensitive material and a layer comprising these compounds(s) as antihalation or filter dye(s) is exposed imagewise and then processed by applying an aqueous alkaline processing composition. After remaining in contact with said alkaline composition for a given time, the colored antihalation or filter dye is discharged by forming a new compound which is substantially colorless and which is different from and non-reversible by pH change to said dye.

For convenience, the specifications of aforementioned applications Ser. Nos. 836,006 now U.S. Pat. No. 4,139,381; and 957,161, now U.S. Pat. No. 4,186,001 are specifically incorporated herein.

As mentioned previously, the preferred compounds of the present invention as represented in formulae III and IV above are initially colored, i.e., they have a light-absorbing form below a given alkaline pH and another light-absorbing form above said alkaline pH. In addition to having an epsilon of at least 4000 in the visible wavelength range in their initially colored form, they preferably also have a λmax above 550 nm.

The epsilon and the λmax for the compounds of Examples 2, 3, 5, 10 and 12 as measured for their initially colored form in trifluoroethanol are set forth in the following Table.

TABLE

| Example | Epsilon | λmax (nm) |
|---------|---------|-----------|
| 2 | 33,900 | 645 |
| 3 | 14,700 | 654 |
| 5 | 8,700 | 613 |
| 10 | 16,500 | 630 |
| 12 | 22,400 | 650 |

For purposes of illustrating the usefulness of the light-screening dye compounds of the present invention, a multicolor photosensitive element using, as the cyan, magenta and yellow dye developers cyan:

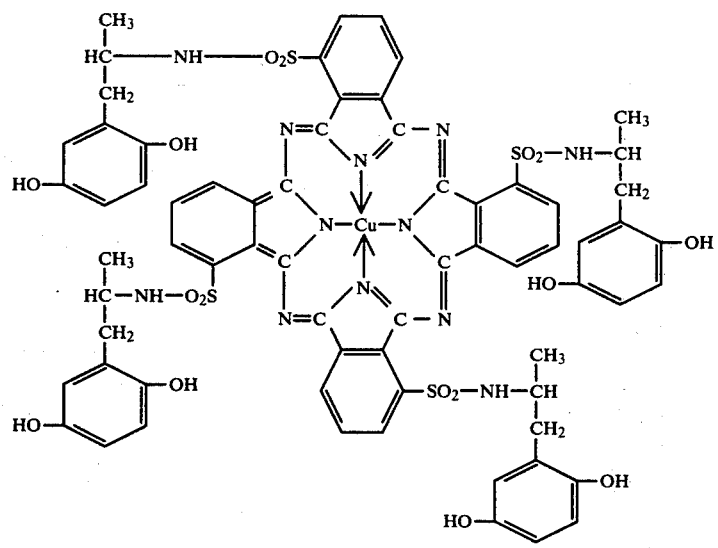

magenta:

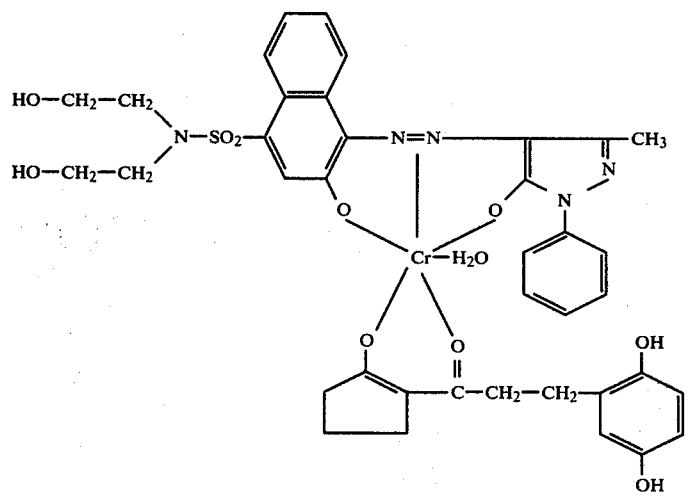

yellow:

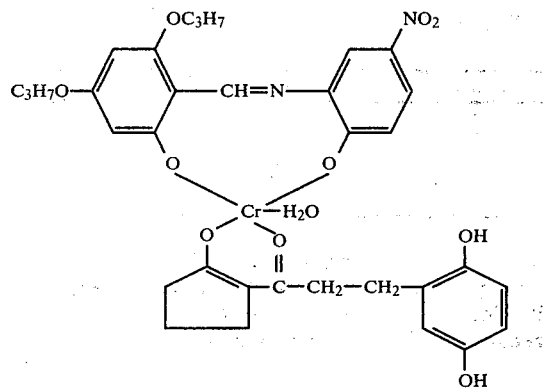

was prepared by coating a gelatin-subcoated 4 mil opaque polyethylene terephthalate film base with the following layers:

1. a layer of cyan dye developer dispersed in gelatin and coated at a coverage of 69 mgs./ft.$^2$ of dye and 138 mgs./ft.$^2$ of gelatin, plus 4'-methylphenyl hydroquinone coated at a coverage of 6.3 mgs./ft.$^2$ and 2-phenylbenzimidazole coated at a coverage of 25.1 mgs./ft.$^2$;

2. a red-sensitive gelatino silver iodobromide emulsion coated at a coverage of 120 mgs./ft.$^2$ of silver halide;

3. a layer of 60-30-4-6 tetrapolymer of butylacrylate, diacetone acrylamide, styrene and methacrylic acid and polyacrylamide coated at a coverage of 232.8 mgs./ft.$^2$ of the copolymer and 7.2 mgs./ft.$^2$ of polyacrylamide;

4. a layer of magenta dye developer dispersed in gelatin and coated at a coverage of 60 mgs./ft.$^2$ of dye and 42 mgs./ft.$^2$ of gelatin; and about 21 mgs./ft.$^2$ of 2-phenylbenzimidazole;

5. a green-sensitive gelatino silver iodobromide emulsion at a coverage of about 74 mgs./ft.$^2$ of silver halide;

6. a layer containing the tetrapolymer referred to above in layer 3 plus polyacrylamide coated at a coverage of 126.9 mgs./ft.$^2$ of tetrapolymer and 8.1 mgs./ft.$^2$ of polyacrylamide; and also containing 6.6 mgs./ft.$^2$ of succindialdehyde;

7. a layer of yellow dye developer dispersed in gelatin and coated at a coverage of 90 mgs./ft.$^2$ of dye and 42 mgs./ft.$^2$ of gelatin; and also containing 19 mgs./ft.$^2$ of 2-phenylbenzimidazole;

8. a blue-sensitive gelatino silver iodobromide emulsion coated at a coverage of 119 mgs./ft.$^2$ of silver and 62 mgs./ft.$^2$ of gelatin; and also containing 19 mgs./ft.$^2$ of 4'-methylphenylhydroquinone; and 9. a layer of gelatin coated at a coverage of 45 mgs./ft.$^2$ of gelatin and also containing carbon black coated at a coverage of 4 mgs./ft.$^2$ A transparent 4 mil polyethylene terephthalate film base was coated, in succession, with the following layers to form an image-receiving component:

1. as a polymeric acid layer, the partial butyl ester of polyethylene/maleic anhydride copolymer at a coverage of about 2,500 mgs./ft.$^2$;

2. a timing layer containing a 14:1 ratio of a 60-30-4-6 tetrapolymer of butylacrylate, diacetone acrylamide, styrene and methacrylic acid and polyvinyl alcohol at a coverage of 500 mgs./ft.$^2$; and 3. a blend of 3 parts by weight of a 2:1 mixture, by weight, of polyvinyl alcohol and poly-4-vinylpyridine and 1 part by weight of a graft copolymer of 4-vinylpyridine and vinylbenzyltrimethylammoniumchloride grafted on hydroxyethyl cellulose in a weight ratio of 2.2/1/2.2, respectively, coated at a coverage of 300 mgs./ft.$^2$ to provide an image-receiving layer.

The aqueous alkaline processing composition comprised the following in % by weight.

| | |
|---|---|
| Water | 49.28 |
| Potassium hydroxide | 5.39 |
| Carboxymethyl hydroxyethyl cellulose | 1.79 |
| Benzotriazole | 0.77 |
| 4-aminopyrazolo-3,4-D-pyrimidine | 0.20 |
| 6-methyluracil | 0.21 |
| N-2-hydroxyethyl-N,N',N'-triscarboxymethyl-ethylene diamine | 0.81 |
| bis(2-aminoethyl)sulfide | 0.02 |
| Polyethylene glycol (mol. wt. 6000) | 0.50 |
| Titanium dioxide | 38.10 |
| Colloidal silica aqueous dispersion (30% SiO$_2$) | 1.68 |
| N-phenethyl-α-picolinium bromide | 1.25 |

To 100 gms. of the above composition was added 1.35 gms. of the pH-sensitive dye of the formula

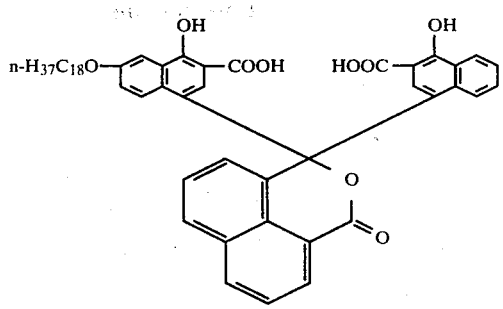

and 0.30 gms. of the pH-sensitive dye of the formula

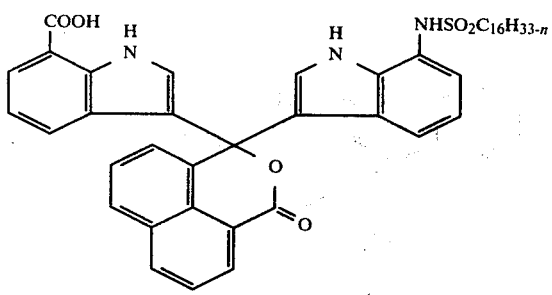 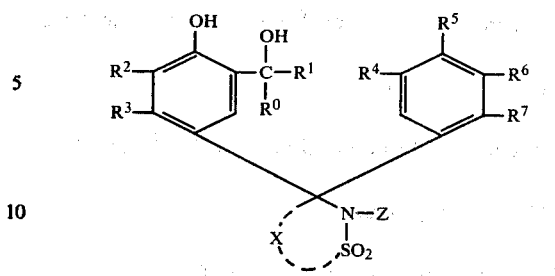

The photosensitive element was exposed to a multicolor stepwedge, the image-receiving element superposed on the exposed photosensitive element, and a rupturable container of the processing composition attached. This assembly was passed between a pair of pressure rolls so that a layer approximately 0.003" thick of the processing composition was distributed between the gelatin overcoat layer 9 of the photosensitive element and the image-receiving layer 3 of the image-receiving element. The blue, green and red D log E curves of the resulting multicolor transfer image (control image) were prepared.

A test multicolor transfer image was prepared in the same manner described above using an identical processing composition and identical photosensitive and image-receiving elements except that the compound prepared in Example 6 above was incorporated in the image-receiving layer 3 at a coverage of 6 mgs./ft.$^2$. The blue, green and red D log E curves of the test image were prepared, and the reflection density for the blue, green and red curves was measured at the 0.75 exposure intercept of the neutral density column for both the control and test multicolor transfer images. The density measurements obtained are set forth in the following Table.

TABLE

| Image | Red | Green | Blue |
|-------|------|-------|------|
| Control | 1.63 | 1.58 | 1.57 |
| Test | 1.48 | 1.55 | 1.54 |

It will be appreciated from reference to the Table that the subject dye was effective in absorbing red light. In addition, it was observed that decolorization of the filter dye in the test image occurred in less than 30 seconds.

Since certain changes may be made in the above product without departing from the scope of the invention herein involved, it is intended that all matter contained in the above description shall be interpreted as illustrative and not in a limiting sense.

What is claimed is:
1. A compound of the formula wherein $R^0$ is perhalomethyl selected from trifluoromethyl, difluoromethyl, difluorochloromethyl, dichlorofluoromethyl, dichloromethyl and trichloromethyl; $R^1$ is selected from hydrogen and perhalomethyl having the same meaning given above; $R^2$ is hydrogen or methyl; $R^3$ is hydrogen, alkyl or alkoxy; $R^2$ and $R^3$ taken together represent the carbon atoms necessary to complete a fused benzene ring; $R^4$ and $R^6$ each are selected from hydrogen, alkyl, alkoxy, chloro and fluoro; $R^7$ is hydrogen, hydroxy, alkyl or alkoxy; $R^6$ and $R^7$ taken together represent the carbon atoms necessary to complete a fused benzene ring provided $R^2$ and $R^3$ are taken separately when $R^6$ and $R^7$ are taken together; $R^5$ is selected from hydrogen, hydroxy, alkyl, alkoxy, —N,N—(dialkyl)amino, —N,N—(ω-$R^8$alkyl)$_2$amino wherein $R^8$ is hydroxy or halo; —NHCOCH$_3$, piperidino, pyrrolidino, N-methylpiperazino, morpholino, thiomorpholino or tetrahydro-2H,4H-1,3,6-dioxazocino; $R^4$, $R^5$ and $R^6$ taken together represent the atoms necessary to complete a fused [ij]quinolizidine ring; Z is a group selected from

wherein R is alkyl having 1 to 7 carbon atoms or phenyl and

wherein Y is hydrogen or an electron-withdrawing group having a positive sigma value greater than 0.6 as defined by Hammett's Equation; and X represents the atoms necessary to complete 2,3-dihydrobenz[d]isothiazole-1,1-dioxide or 2,3-dihydronaphtho[1,8-de]-1,2-thiazine-1,1-dioxide.

2. A compound as defined in claim 1 wherein $R^1$ is hydrogen.

3. A compound as defined in claim 1 wherein $R^1$ is perhalomethyl.

4. A compound as defined in claim 1 wherein $R^2$ and $R^3$ taken together represent the carbon atoms necessary to complete a fused benzene ring.

5. A compound as defined in claim 1 wherein $R^2$ and $R^3$ are hydrogen.

6. A compound as defined in claim 1 wherein $R^4$, $R^5$ and $R^6$ taken together represent the atoms necessary to complete a fused [ij]quinolizidine ring and $R^7$ is hydrogen.

7. A compound as defined in claim 1 wherein $R^4$, $R^6$ and $R^7$ are hydrogen.

8. A compound as defined in claim 7 wherein $R^5$ is —N,N—(dialkyl)amino.

9. A compound as defined in claim 7 wherein $R^5$ is —N,N—(ω-$R^8$alkyl)$_2$amino.

10. A compound as defined in claim 1 wherein $R^4$ and $R^6$ are hydrogen, $R^5$ is —N,N—(dialkyl)amino and $R^7$ is alkyl.

11. A compound as defined in claim 1 wherein R is said alkyl.

12. A compound as defined in claim 1 wherein Y is said electron-withdrawing group.

13. The compound

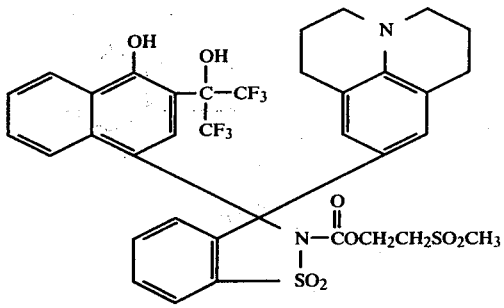

14. The compound

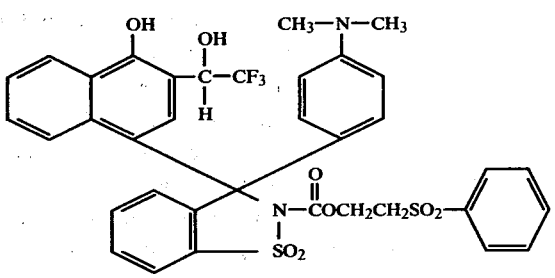

* * * * *